United States Patent
Cheng et al.

(10) Patent No.: US 10,799,120 B2
(45) Date of Patent: Oct. 13, 2020

(54) IMAGE PROCESSING METHOD AND DEVICE FOR FLUORESCENCE REACTION REGION OF TEETH

(71) Applicant: Quanta Computer Inc., Taoyuan (TW)

(72) Inventors: Kai-Ju Cheng, Taoyuan (TW); Chin-Yuan Ting, Taoyuan (TW); Hsin-Lun Hsieh, Taoyuan (TW); Tsung-Hsin Lu, Taoyuan (TW); Yu-Hsun Chen, Taoyuan (TW); Hao-Ping Lee, Taoyuan (TW)

(73) Assignee: QUANTA COMPUTER INC., Guishan Dist., Taoyuan (TW)

( * ) Notice: Subject to any disclaimer, the term of this patent is extended or adjusted under 35 U.S.C. 154(b) by 93 days.

(21) Appl. No.: 16/217,112

(22) Filed: Dec. 12, 2018

(65) Prior Publication Data
US 2020/0069188 A1  Mar. 5, 2020

(30) Foreign Application Priority Data
Aug. 30, 2018  (TW) .............................. 107130212 A

(51) Int. Cl.
*G06K 9/00* (2006.01)
*A61B 5/00* (2006.01)
(Continued)

(52) U.S. Cl.
CPC .............. *A61B 5/0088* (2013.01); *A61B 1/04* (2013.01); *A61B 1/06* (2013.01); *A61B 1/24* (2013.01);
(Continued)

(58) Field of Classification Search
CPC ....... A61B 1/00009; A61B 1/04; A61B 1/043; A61B 1/06; A61B 1/24; A61B 5/0071;
(Continued)

(56) References Cited

U.S. PATENT DOCUMENTS

| | | | | |
|---|---|---|---|---|
| 4,703,441 A | * | 10/1987 | Kishi | G05B 19/409 345/530 |
| 7,613,505 B2 | * | 11/2009 | Mazuir | A61B 5/0088 600/476 |

(Continued)

FOREIGN PATENT DOCUMENTS

| | | |
|---|---|---|
| WO | 8404979 A1 | 12/1984 |
| WO | 2014125037 A1 | 8/2014 |

OTHER PUBLICATIONS

TIPO Office Action dated May 31, 2019, TW Application No. 107130212, pp. 1-5.
(Continued)

*Primary Examiner* — Charles T Shedrick
(74) *Attorney, Agent, or Firm* — McClure, Qualey & Rodack, LLP

(57) ABSTRACT

An image processing method for a fluorescence reaction region of teeth. The image processing method includes emitting blue light from a light source to illuminate the teeth in a mouth, so that the teeth generate fluorescence; capturing a first teeth image of the teeth by an image capturing unit; separating the first teeth image into a first red-value image, a first green-value image, and a first blue-value image by a processing unit; transforming the first red-value image into a second red-value image by the processing unit using a pixel value transforming function; and combining the second red-value image, the first green-value image, and the first blue-value image into a second teeth image by the processing unit.

7 Claims, 8 Drawing Sheets
(2 of 8 Drawing Sheet(s) Filed in Color)

(51) Int. Cl.
*A61B 1/04* (2006.01)
*A61B 1/06* (2006.01)
*A61B 1/24* (2006.01)
*G06T 11/00* (2006.01)

(52) U.S. Cl.
CPC .......... *A61B 5/0071* (2013.01); *G06T 11/001* (2013.01); *G06T 2210/41* (2013.01)

(58) Field of Classification Search
CPC ............... A61B 5/0088; G06T 11/001; G06T 2207/30004; G06T 2210/41
USPC ........................................................ 382/128
See application file for complete search history.

(56) References Cited

U.S. PATENT DOCUMENTS

| | | | |
|---|---|---|---|
| 10,383,711 B2* | 8/2019 | Esbech | G01B 11/2513 |
| 2005/0283065 A1 | 12/2005 | Babayoff et al. | |
| 2007/0248931 A1* | 10/2007 | Wong | A61B 5/0088 433/29 |
| 2009/0135455 A1 | 5/2009 | Li et al. | |
| 2009/0185712 A1* | 7/2009 | Wong | G06T 7/187 382/100 |
| 2010/0216087 A1 | 8/2010 | Hennig et al. | |
| 2012/0301053 A1* | 11/2012 | Watanabe | G06T 7/11 382/298 |
| 2016/0125601 A1* | 5/2016 | Wu | G06T 7/0012 382/128 |

OTHER PUBLICATIONS

Extended European Search Report dated Aug. 13, 2019, EP Application No. 19151449.6, pp. 1-7.

* cited by examiner

IMAGE PROCESSING METHOD AND DEVICE FOR FLUORESCENCE REACTION REGION OF TEETH

CROSS REFERENCE TO RELATED APPLICATIONS

This Application claims priority of Taiwan Patent Application No. 107130212, filed on Aug. 30, 2018, the entirety of which is incorporated by reference herein.

BACKGROUND

Field of the Invention

The present disclosure relates to an image processing method and an image processing device for a fluorescence reaction region of teeth, and, in particular, to an image processing method and an image processing device that can adjust the red-value image of an image of the fluorescence reaction region of teeth.

Description of the Related Art

Dental plaque can cause many adverse effects on teeth, such as calculus, gingivitis, periodontal disease, and tooth decay. It is important to have regular dental examinations to detect whether teeth have dental plaque. However, dental plaque is not easily detected by the naked eye. Therefore, various dental plaque detection methods have been used to help detect dental plaque on teeth.

Methods for detecting dental plaque typically utilize a fluorescence reaction of the dental plaque. For example, the detection of dental plaque typically uses light with a low wavelength to illuminate teeth. If there is dental plaque on the teeth, the region of the teeth having dental plaque will generate a red fluorescence. In order to detect the dental plaque on the teeth more quickly and accurately, a teeth image with the dental plaque on the teeth can be adjusted to make the red fluorescence of the dental plaque more obvious.

BRIEF SUMMARY

The present disclosure provides an image processing method for a fluorescence reaction region of teeth. The method includes emitting blue light from a light source to illuminate the teeth in a mouth, so that the teeth generate fluorescence; capturing a first teeth image of the teeth by an image capturing unit; separating the first teeth image into a first red-value image, a first green-value image, and a first blue-value image by a processing unit; transforming the first red-value image into a second red-value image by the processing unit using a pixel value transforming function; and combining the second red-value image, the first green-value image, and the first blue-value image into a second teeth image by the processing unit.

The present disclosure provides an image processing device for a fluorescence reaction region of teeth. The image processing device includes a light source, disposed to emit blue light to illuminate the teeth in a mouth, so that the teeth generate fluorescence; an image capturing unit, disposed to capture a first teeth image of the teeth; a processing unit, disposed to process the first teeth image. The step in which the processing unit processes the first teeth image includes separating the first teeth image into a first red-value image, a first green-value image, and a first blue-value image; transforming the first red-value image into a second red-value image by using a pixel value transforming function; and combining the second red-value image, the first green-value image, and the first blue-value image into a second teeth image.

BRIEF DESCRIPTION

In order to describe the manner in which the above-recited and other advantages and features of the disclosure can be obtained, a more particular description of the principles briefly described above will be rendered by reference to specific examples thereof which are illustrated in the appended drawings. Understanding that these drawings depict only exemplary aspects of the disclosure and are not therefore to be considered to be limiting of its scope, the principles herein are described and explained with additional specificity and detail through the use of the accompanying drawings.

The patent or application file contains at least one drawing executed in color. Copies of this patent or patent application publication with color drawing(s) will be provided by the Office upon request and payment of the necessary fee.

DETAILED DESCRIPTION

Figure 1:
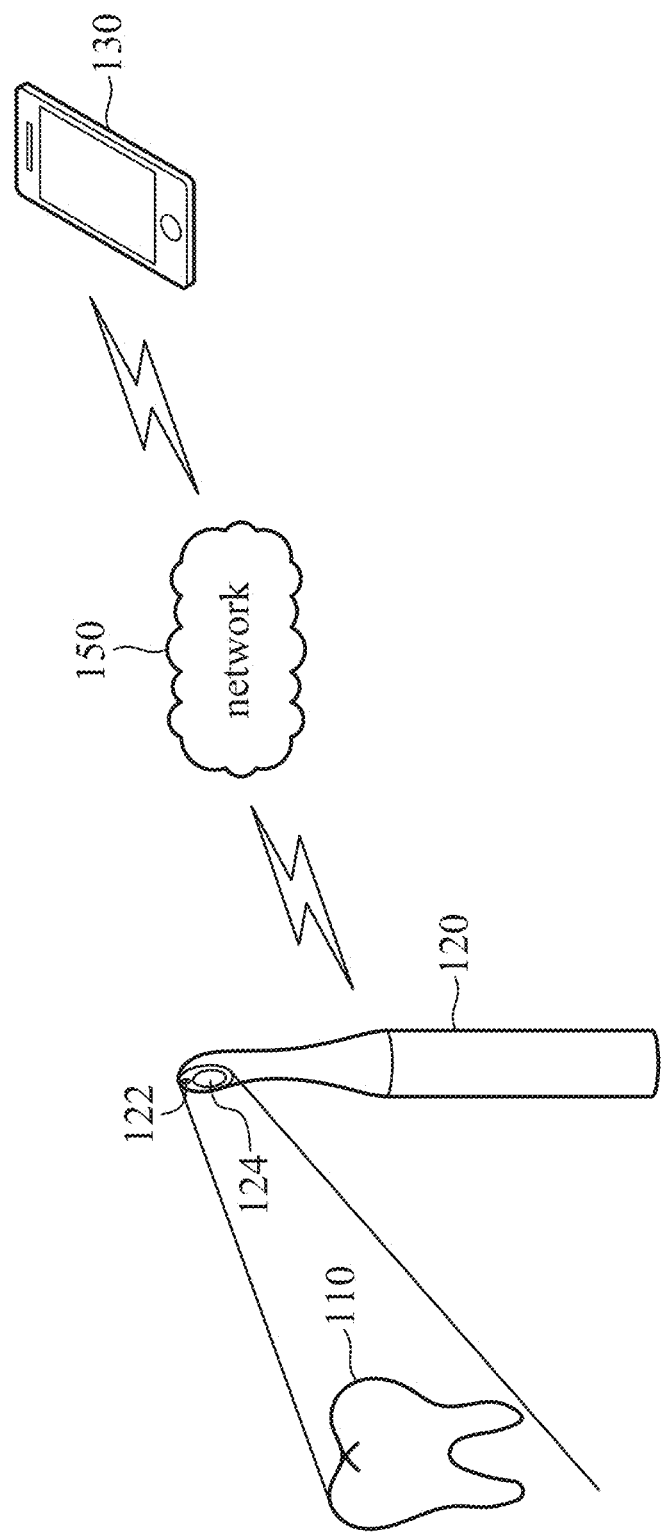
FIG. 1 illustrates an operation of an image processing device for a fluorescence reaction region of teeth, in accordance with some embodiments of the present disclosure.

The present inventions can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at, near, or nearly at," or "within 3-5% of,"

or "within acceptable manufacturing tolerances," or any logical combination thereof, for example.

FIG. 1 illustrates an operation of an image processing device 120 for a fluorescence reaction region of teeth, in accordance with some embodiments of the present disclosure. As shown in FIG. 1, the image processing device 120 includes a light source 122 and an image capturing unit 124. The light source 122 of the image processing device 120 generates (or emits) light with a low wavelength to illuminate teeth 110 in the mouth. If there is dental plaque on the teeth 110, a fluorescence reaction will occur on the teeth having dental plaque to generate a red fluorescence.

In some embodiments, the light source 122 is a light-emitting diode (LED). The light emitted from the light source 122 may include blue light, violet light, or ultraviolet light (UV). As discussed above, when the light from the light source 122 is used to illuminate the teeth 110, the fluorescence reaction will occur on the teeth having dental plaque to generate a red fluorescence.

The image capturing unit 124 is disposed to capture an image of the teeth 110 (i.e., the teeth image). After the teeth image is captured, the image processing device 120 processes the teeth image. In the present embodiment, the red pixel value of the red-value image of the teeth image will be adjusted, which are described below. The image processing device 120 then transmits the processed teeth image to the electronic device 130 via the network 150, so that an electronic device 130 having a display device can display the processed teeth image.

The electronic device 130 may include a desktop computer, a notebook, a smartphone, a personal digital assistant (PDA), a tablet, or any other device having a display screen. The user may view the dental plaque in the processed teeth image through the electronic device 130.

The network 150 can provide wired and/or wireless networks. The network 150 may also include a local area network (LAN) (e.g., an intranet), a wireless local area network (WLAN) or a Wi-Fi network, a third generation (3G) or a fourth generation (4G) mobile telecommunications network, a wide area network (WAN), the Internet, Bluetooth, or any suitable combination thereof.

In this embodiment, the light source 122 is integrated into the image processing device 120. In other embodiments, it should be understood that the image processing device 120 may not have a light source 122 and an external light source may be used to illuminate the teeth 110 in the teeth.

In the present embodiment, the image processing device 120 may be a detection device for detecting the dental plaque on the teeth. For example, the image processing device 120 can be a dental mirror, but it should be understood by those skilled in the art that the present disclosure is not limited thereto.

Figure 2:
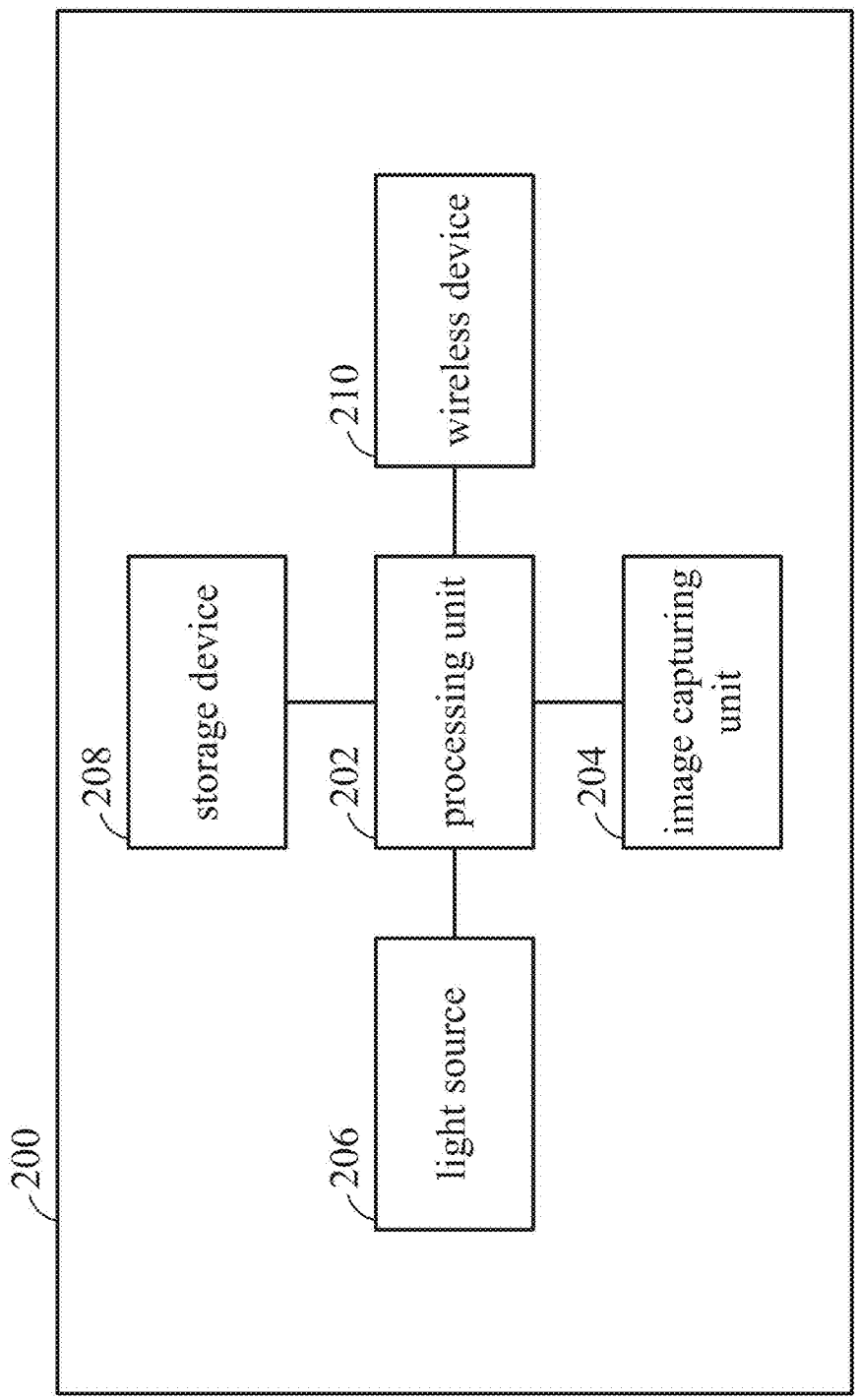
FIG. 2 illustrates an image processing device for a fluorescence reaction region of teeth, in accordance with some embodiments of the present disclosure.

FIG. 2 illustrates an image processing device 200 for a fluorescence reaction region of teeth, in accordance with some embodiments of the present disclosure. The image processing device 200 includes a processing unit 202, an image capturing unit 204, a light source 206, a storage device 208, and a wireless device 210. It should be understood that other configurations and inclusion or omission of various items in the image processing device 200 may be possible. The image processing device 200 is exemplary, and is not intended to limit the disclosure beyond what is explicitly recited in the claims.

The image capturing unit 204 is connected to the processing unit 202. The image capturing unit 204 is disposed to capture or shoot the teeth image. In the present embodiment, the teeth image captured by the image capturing unit 204 is also referred to as a first teeth image: that is, an original teeth image that has not undergone an image processing procedure.

The light source 206 is connected to the processing unit 202. The light source 206 may include a light-emitting diode (LED). The light emitted from the light source 206 may include blue light, violet light, or ultraviolet light (UV). Specifically, the light source 206 can generate light having a wavelength in the range of 370 to 430 nanometers (nm). In another embodiment, light source 206 can emit the light having a wavelength of 405 nanometers (nm). In the present embodiment, when the light having the specific wavelength range generated by the light source 206 is used to illuminate the teeth, the fluorescence reaction will occur on the teeth having dental plaque to generate a red fluorescence.

The storage device 208 is connected to the processing unit 202. The storage device 208 is a non-volatile memory and can be a hard disk or another type of computer readable media. The media can store data that are accessible by a computer, such as magnetic cassettes, flash memory cards, solid state memory devices, digital versatile disks, cartridges, random access memories (RAMs), read only memory (ROM), and hybrids thereof. In the present embodiment, the storage device 208 stores a pixel value transforming function and a red pixel value correspondence table (which will be described below in detail).

The wireless device 210 is connected to the processing unit 202. The wireless device 210 transmits the teeth image processed by the processing unit 202 to an electronic device (e.g., the electronic device 130) having the display device through a network (e.g., the network 150), so that the electronic device can display the processed teeth image. The user can observe the dental plaque on the teeth 110 of the processed teeth image through the electronic device.

The processing unit 202 may essentially be a completely self-contained computing system, containing multiple cores or processors, a bus, memory controller, cache, etc. A multi-core processor may be symmetric or asymmetric. The processing unit 202 can be used to perform image process to the teeth image. In the present embodiment, the processed teeth image is also referred to as a second teeth image.

The image processing, the pixel value transforming function, and the red pixel value correspondence table of the embodiments of the present disclosure will be described below.

In the present embodiment, the processing unit 202 performs image processing to the teeth image (also referred to as the first teeth image) captured by the image capturing unit 204. After the processing unit 202 receives the first teeth image, the processing unit 202 separates the first teeth image into a first red-value image, a first green-value image, and a first blue-value image.

RGB is a color model constructed from red, green, and blue. These colors (red, green and blue) are also called the three primary colors of light. The red, green and blue light can be added together in various ways with different intensities (brightness) to reproduce a broad array of colors.

An image is composed of a number of "pixels", and each of the pixels represents a color that can be composed of different respective intensities of red, green, and blue. Therefore, the pixel color of the image can be represented by an RGB value (also referred to as the pixel value). In the RGB value, the intensity of red, green, and blue is typically represented by a range of 0 to $2^n-1$, where n represents a bit value of a positive integer. For example, in the present embodiment, the intensity of the color (color value or pixel value) is represented by 8 bits, so that the intensities of red, green, and blue each have a range of 0 to 255.

After obtaining the RGB values of all the pixels in the image, the red, green, and blue value of each RGB values can be separated (a RGB value of a pixel is separated into a red pixel value, a green pixel value, and a blue pixel value), thereby obtaining a red-value image, a green-value image, and a blue-value image of the image. In the present embodiment, after the RGB values of the first teeth image are obtained, the first teeth image is separated into a first red-value image, a first green-value image, and a first blue-value image.

Since the teeth that have dental plaque are illuminated by the light source to generate a "red" fluorescence, the red pixel value of the dental plaque region is large in the first teeth image. In the present embodiment, a predetermined value is set in the processing unit 202 (or the storage device 208). The red pixel values that are greater than the predetermined value in the first red-value image of the first teeth image may indicate the presence of dental plaque and the red pixel values that are smaller than the predetermined value may indicate that there is no dental plaque.

The storage device 208 stores a pixel value transforming function. In the first red-value image, the red pixel value that is greater than the predetermined value is increased and the red pixel value that is smaller than the predetermined value is decreased by using the pixel value transforming function, so that the first red-value image is transformed into a second red-value image. The processing unit 202 then combines the second red-value image, the first green-value image, and the first blue-value image into a second teeth image (i.e., the processed teeth image discussed above).

In the second teeth image, the red pixel value of the region with the dental plaque is increased (i.e., the region having the dental plaque becomes redder (the intensity or the brightness increased)), and the red pixel value of the region without the dental plaque is decreased (i.e., the region without the dental plaque becomes less red (the intensity or the brightness decreased)). Therefore, the user can more easily know, though direct observation, where there is dental plaque in the second teeth image and reduce misjudgment.

The pixel value transforming function includes two functions L(x) and R(x), L(x) is used to decrease the red pixel value, and R(x) is used to increase the red pixel value. L(x) and R(x) are shown below:

$L(x)=x-A(x)$, x is the original red pixel value, and the range of x is from 0 to 128;

$R(x)=x+B(x)$, x is the original red pixel value, and the range of x is from 128 to 255;

where A(x) is a function of the decreased value of the red pixel value and B(x) is a function of the increased value of the red pixel value. In the present embodiment, the predetermined value is 128. Therefore, the (original) red pixel value that is greater than 128 is increased and the red pixel value less than 128 is decreased. In some embodiments, the decreased value of the red pixel value is also referred to as a first transformed red pixel value, and the increased value of the red pixel value is also referred to as a second transformed red pixel value.

A(x) and B(x) are shown below:

$$A(x): \frac{(x-64)^2}{64^2} + \frac{(y)^2}{k1^2} = 1$$

Figure 3:
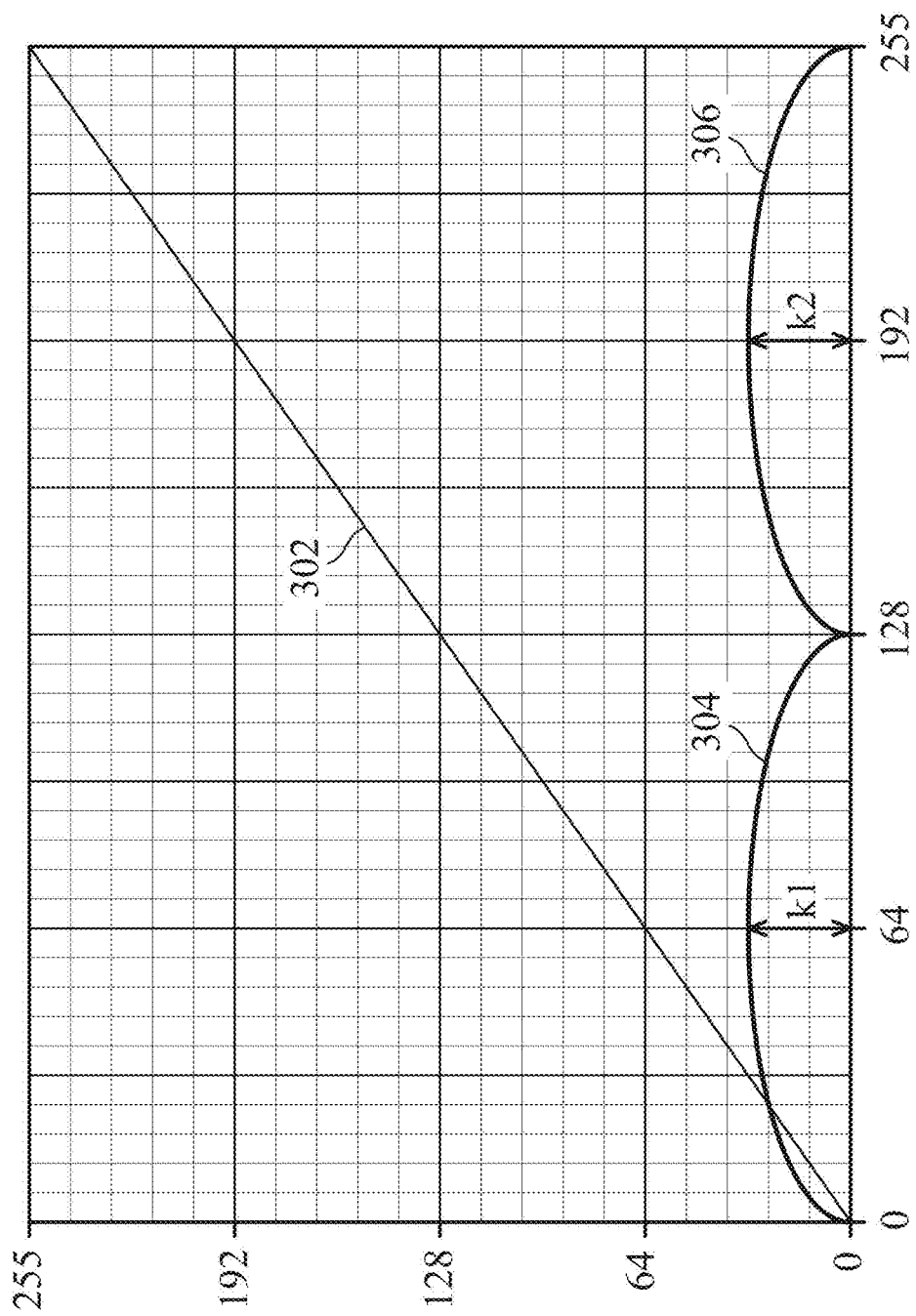
FIG. 3 is a graph of the elliptic functions A(x) and B(x), in accordance with some embodiments of the present disclosure.

-continued $$B(x): \frac{(x-192)^2}{64^2} + \frac{(y)^2}{k2^2} = 1$$

where the range of x in A(x) is from 0 to 128, and the range of x in B(x) ranges is from 128 to 255. The parameters k1 and k2 are adjustable. As shown in the above function, A(x) and B(x) are shown as elliptic functions. After substituting the original red pixel value x into A(x) (or B(x)), a decreased value (or increased value) y can be obtained. The parameters k1 and k2 also represent the short axis length of the ellipse (e.g., k1 and k2 in FIG. 3). The decreased value and the increased value (y) are adjustable by adjusting k1 and k2. In A(x) and B(x), the "64" in the denominator represents the long axis length of the ellipse. The "64" and "192" in the numerator represent the center point position of the ellipse on the X axis, as shown in FIG. 3. In some embodiments, the decreased value calculated by A(x) is also referred to as a first transformed red pixel value, and the increased value calculated by B(x) is also referred to as a second transformed red pixel value.

FIG. 3 is a graph of the elliptic functions A(x) and B(x), in accordance with some embodiments of the present disclosure. In this embodiment, the range of the red pixel value is from 0 to 255 (the intensity of the color (color value or pixel value) is represented by 8 bits). The X axis represents the original red pixel value, the Y axis represents the adjusted red pixel value, and the line segment 302 is the unadjusted red pixel value (x=y). The curve 304 is a graph of A(x), where the range of x is from 0 to 128 and k1 is 32. The curve 306 is a graph of B(x), where the range of x is from 128 to 255 and k2 is 32. In this embodiment, the intensity of the color (color value or pixel value) is represented by 8 bits, so that the lower limit of the pixel value is 0 and the upper limit of the pixel value is 255. In some embodiments, the intensity of the color is represented by n bits, and the upper limit of the pixel value is 2n−1, where n is a positive integer.

As shown in FIG. 3, the curves 304 and 306 are graphs of A(x) and B(x), and the y values of the curve 304 are the decreased value and the y values of the curve 306 are the increased value. Therefore, by combining the line segment 302 with curves 304 and 306, a graph of the pixel value transforming function can be obtained. For example, as with the pixel value transforming function discussed above, the y value which the x value less than 128 in the line segment 302 is subtracted the y value of the curve 304, and the y value which the x value that is greater than 128 in the line segment 302 is added the y value of the curve 306, so that a graph of the pixel value transforming function can be obtained (as shown in FIG. 4).

Figure 4:
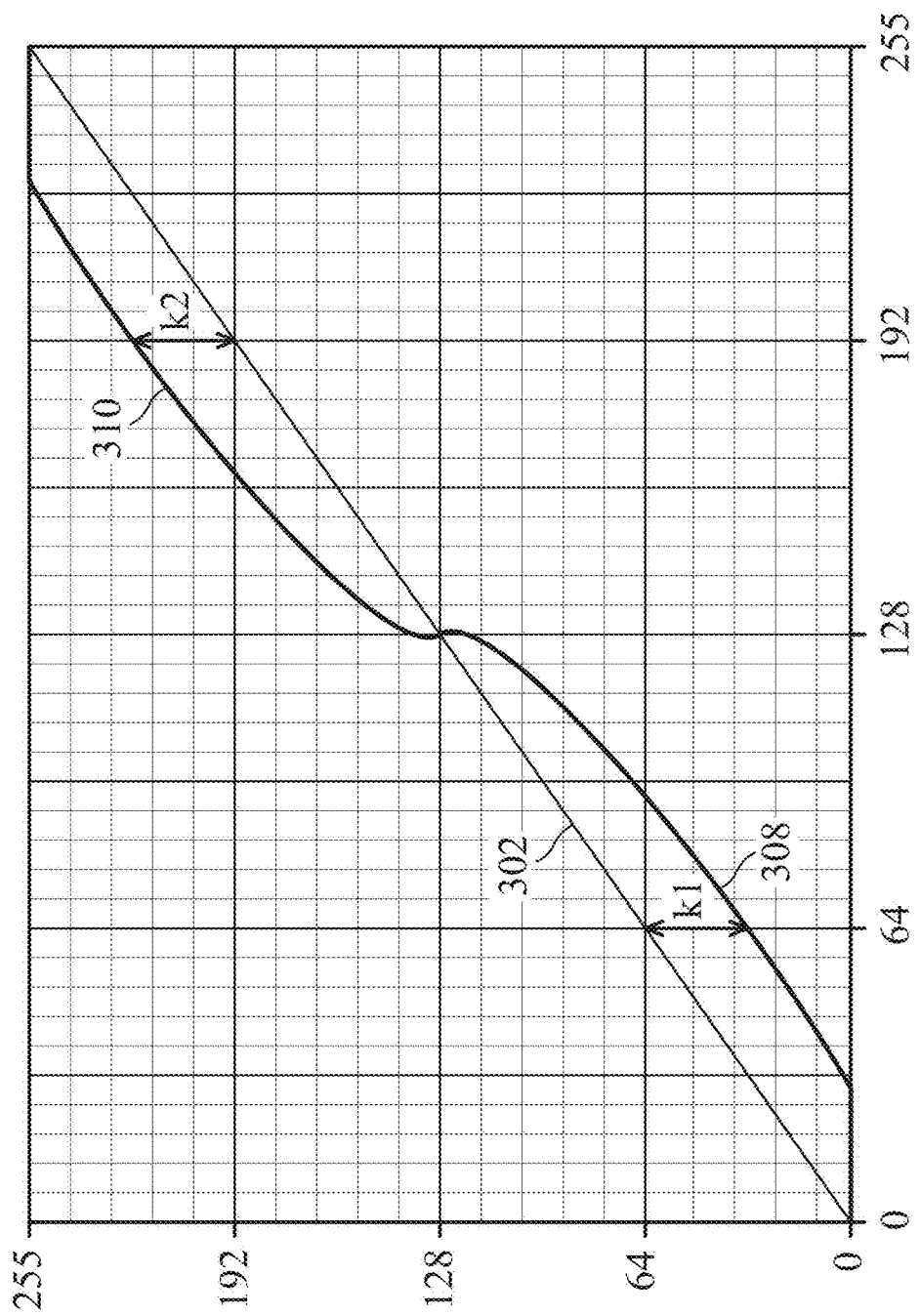
FIG. 4 is a graph of the pixel value transforming function, in accordance with some embodiments of the present disclosure.

FIG. 4 is a graph of the pixel value transforming function, in accordance with some embodiments of the present disclosure. The curve 308 is the line segment 302 (x value less than 128) minus the curve 304, and the curve 310 is the line segment 302 (x value that is greater than 128) plus the curve 306. The curves 308 and 310 are combined into the graph of the pixel value transforming function. In other words, the curve 308 is the graph of L(x), and the curve 310 is the graph of R(x), and both L(x) and R(x) are combined into the pixel value transforming function. According to the graph of the pixel value transforming function, it can be obtained how the original red pixel value is decreased or increased by using the pixel value conversion function. For example, in an original red-value image of an image (e.g., the first red-value image of the first teeth image), the red pixel value 192

(greater than 128) is transformed into the red pixel value 224 by using the pixel value transforming function.

As discussed above with FIGS. 3 and 4, the predetermined value is 128, so that the red pixel value that is greater than 128 is increased, and the red pixel value less than 128 is decreased. In some embodiments, the predetermined value can be adjusted. Similarly, the red pixel value that is greater than the predetermined value is increased, and the red pixel value that is smaller than the predetermined value is decreased.

Figure 5:
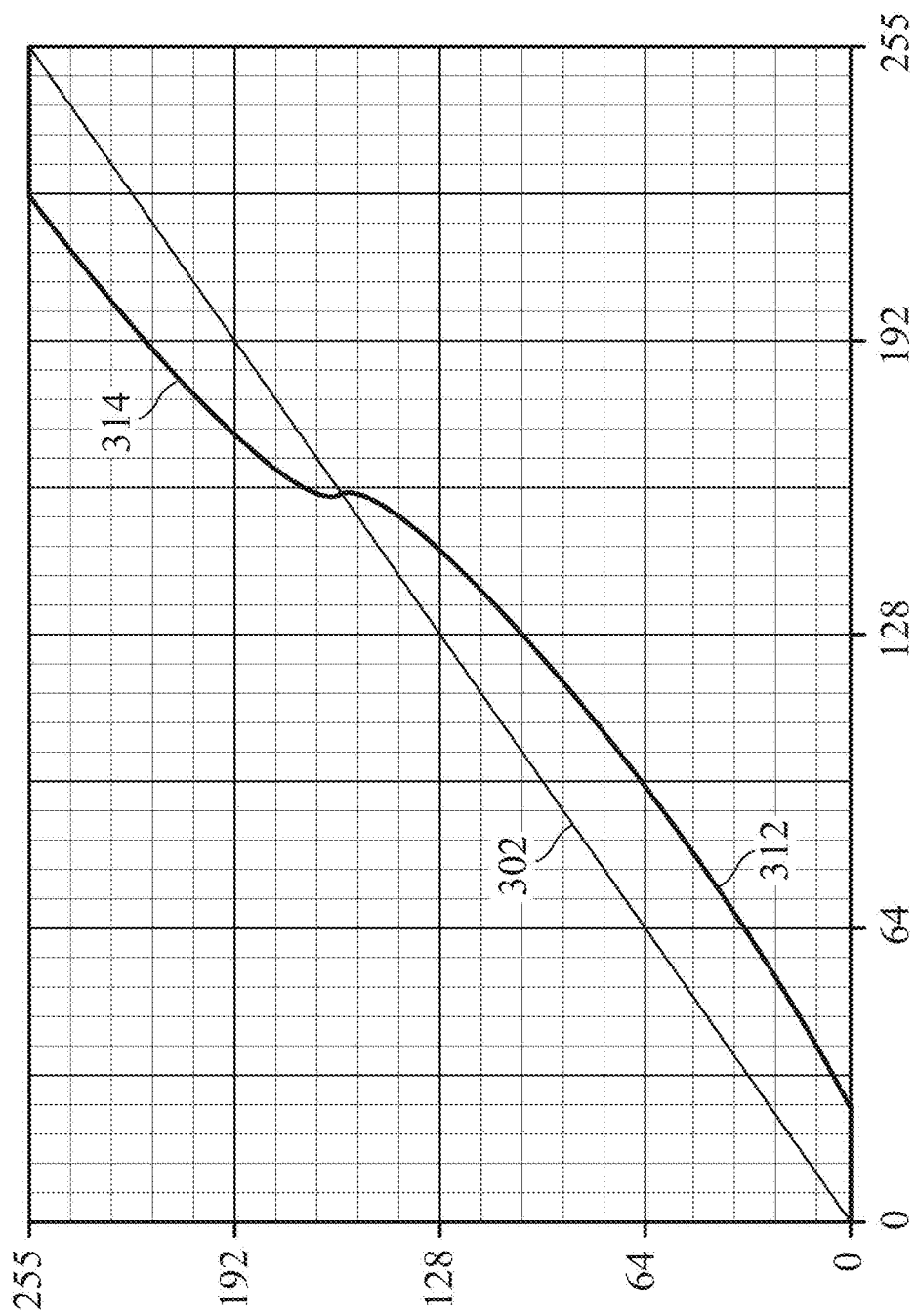
FIG. 5 is a graph of the pixel value transforming function having another predetermined value, in accordance with some embodiments of the present disclosure.

FIG. 5 is a graph of the pixel value transforming function having another predetermined value, in accordance with some embodiments of the present disclosure. In this embodiment, the predetermined value is 160. Similarly, the red pixel value that is greater than 160 is increased, and the red pixel value that is smaller than 160 is decreased. It should be understood that other parameters in the pixel value transforming function can also be adjusted. For example, the functions corresponding to curves 312 and 314 in FIG. 5 (i.e., L(x) and R(x)) are shown below:

$L(x)=x-A(x)$, x is the original red pixel value, and the range of x is from 0 to 160;

$R(x)=x+B(x)$, x is the original red pixel value, and the range of x is from 160 to 255;

where the A(x) and B(x) are shown below:

$$A(x): \frac{(x-80)^2}{80^2} + \frac{(y)^2}{32^2} = 1$$

$$B(x): \frac{(x-208)^2}{48^2} + \frac{(y)^2}{32^2} = 1$$

Therefore, the various parameters in the pixel value transforming function (i.e., any numbers other than x, y in A(x) and B(x)) can be adjusted to obtain different transformed results of the pixel value.

By using the pixel value transforming function, the original red-value image of the teeth image (e.g., the first red-value image of the first teeth image) is transformed into a processed red-value image (e.g., the second red-value image of the first teeth image). Then, the processed red-value image, the original green-value image (e.g., the first green-value image of the first teeth image), and the original blue-value image (e.g., the first blue-value image of the first teeth image) are combined into a processed image (e.g., the second teeth image).

As discussed above, the storage device 208 may store a red pixel value correspondence table. In some embodiments, the processing unit 202 transforms the original red-value image into the processed red-value image by using the red pixel value correspondence table instead of directly transforming the original red-value image into the processed red-value image by using the pixel value transforming function.

The following table shows the red pixel value correspondence table:

| original red pixel value | transformed red pixel value |
|---|---|
| 0 | 0 |
| 1-8 | 0 |
| 9-10 | 1 |
| 11-63 | 2-47 |
| 64 | 48 |

-continued

| original red pixel value | transformed red pixel value |
|---|---|
| 65-127 | 46-124 |
| 128 | 128 |
| 129-192 | 132-208 |
| 192 | 208 |
| 193-245 | 209-254 |
| 246-255 | 255 |
| 255 | 255 |

As shown in the above table, the predetermined value is 128, the red pixel value that is greater than 128 is increased, and the red pixel value that is smaller than 128 is decreased. In some embodiments, the red pixel value correspondence table is obtained by using a pixel value transforming function. For example, the above table can be obtained by using the pixel value transforming function shown below:

$L(x)=x-A(x)$, x is the original red pixel value, and the range of x is from 0 to 128;

$R(x)=x+B(x)$, x is the original red pixel value, and the range of x is from 128 to 255;

where the A(x) and B(x) are shown below:

$$A(x): \frac{(x-64)^2}{64^2} + \frac{(y)^2}{16^2} = 1$$

$$B(x): \frac{(x-192)^2}{64^2} + \frac{(y)^2}{16^2} = 1$$

Therefore, the red pixel value correspondence table can be obtained by transforming the red pixel value of 0 to 255 using the pixel value transforming function. In some embodiments, the red pixel value correspondence table is obtained by the processing unit 202 using the pixel value transforming function first, and stored in the storage device 208. When the image processing device 200 is used later, the processing unit 202 then transforms the first red-value image into the second red-value image according to the red pixel value correspondence table.

Figure 6A:
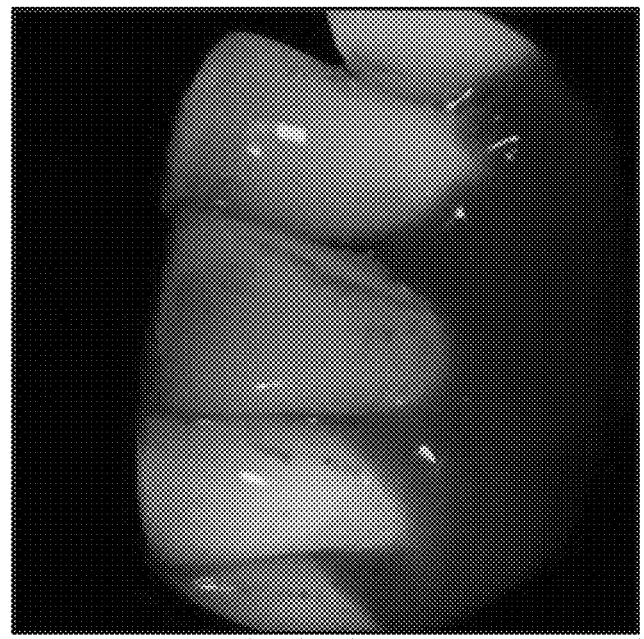
FIGS. 6A and 6C illustrate the teeth images before image processing, in accordance with some embodiments of the present disclosure.
Figure 6B:
FIGS. 6B and 6D illustrate the teeth images after image processing, in accordance with some embodiments of the present disclosure.
Figure 6C:
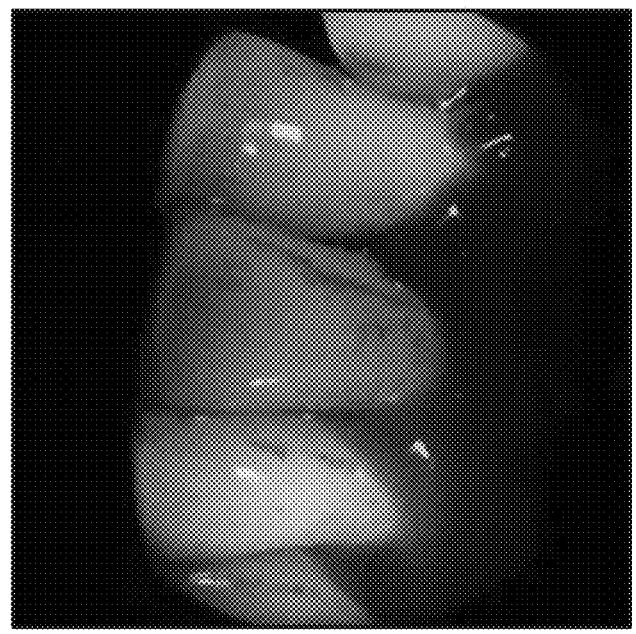
Figure 6D:
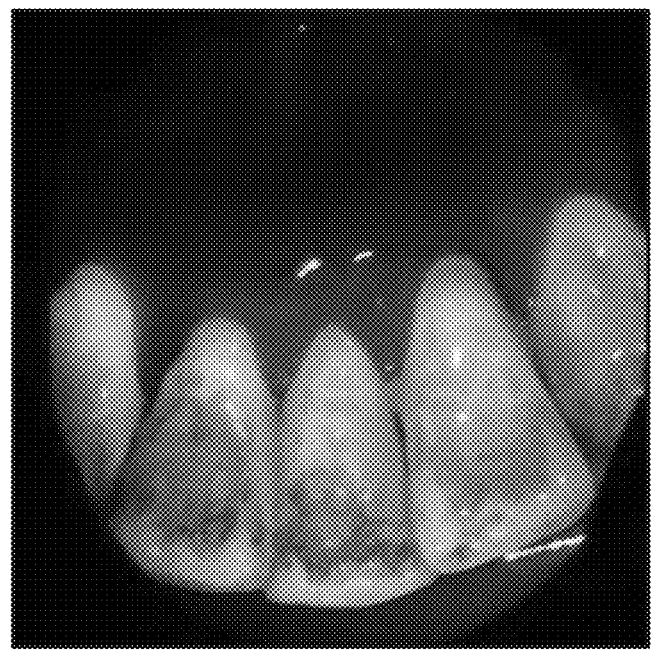

FIGS. 6A to 6D illustrate the teeth images before image processing and after image processing, in accordance with some embodiments of the present disclosure. FIGS. 6A and 6C are teeth images before image processing. FIGS. 6B and 6D are teeth images after image processing. The teeth image of FIG. 6B is the image processing result of the teeth image of FIG. 6A (i.e., FIG. 6A is the first teeth image, and FIG. 6B is the second teeth image). The teeth image of FIG. 6D is the image processing result of the teeth image of FIG. 6C (i.e., FIG. 6C is the first teeth image, and FIG. 6D is the second teeth image).

As shown in FIGS. 6A and 6C, there is dental plaque on the teeth in the teeth image and the dental plaque shows red fluorescence. Then, according to the present embodiment, the image processing is performed to the teeth images of FIGS. 6A and 6C to obtain the processed teeth image (the teeth images of FIGS. 6B and 6D). As shown in FIGS. 6B and 6D, the red pixel value on the teeth having dental plaque is increased (the intensity (or brightness) of red is increased), and the red pixel value on the teeth without the dental plaque is decreased (the intensity (or brightness) of red is decreased).

Figure 7:
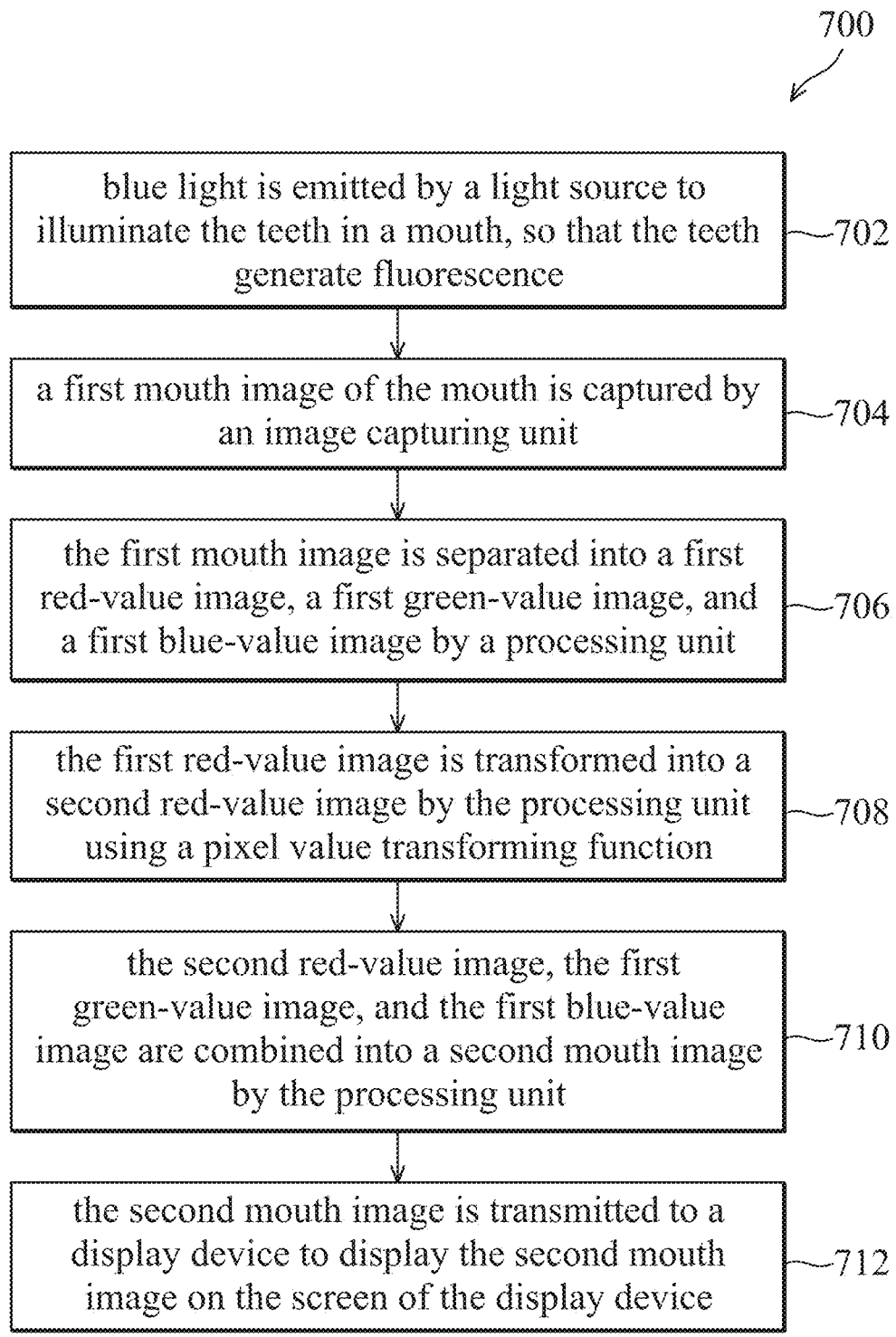
FIG. 7 illustrates a flowchart of the image processing method for a fluorescence reaction region of teeth, in accordance with some embodiments of the present disclosure.

FIG. 7 illustrates a flowchart of the image processing method 700 for a fluorescence reaction region of teeth, in accordance with some embodiments of the present disclosure. In operation 702, blue light is emitted by a light source to illuminate the teeth in a mouth, so that the teeth generate fluorescence. If there is dental plaque on the teeth, a fluorescence reaction will occur on the teeth having dental plaque to generate a red fluorescence. For example, the light source 122 emits light having a low wavelength (blue light) to illuminate teeth 110 in the mouth such, so that the teeth having dental plaque generate fluorescence.

In operation 704, a first teeth image of the teeth is captured by an image capturing unit. For example, the image capturing unit 204 captures the first teeth image in the mouth. In the present embodiment, the first teeth image is an original teeth image that has not undergone any image processing procedure.

In operation 706, the first teeth image is separated into a first red-value image, a first green-value image, and a first blue-value image by a processing unit. For example, after the processing unit 202 receives the first teeth image, the processing unit 202 separates the first teeth image into the first red-value image, the first green-value image, and the first blue-value image.

In operation 708, the first red-value image is transformed into a second red-value image by the processing unit using a pixel value transforming function. The pixel value transforming function includes a predetermined value. The red pixel value of the first red-value image that is greater than the predetermined value is increased by the processing unit and the red pixel value that is smaller than a predetermined value is decreased by the processing unit, so that the first red-value image is transformed into the second red-value image.

In some embodiments, the processing unit makes a red pixel value correspondence table by using the pixel value transforming function and the red pixel value of 0 to 255 and stores the pixel value transforming function in a storage device at first. The processing unit then transforms the first red-value image into the second red-value image according to the red pixel value correspondence table.

In operation 710, the second red-value image, the first green-value image, and the first blue-value image are combined into a second teeth image by the processing unit. In the present embodiment, the second teeth image is the processed teeth image.

In operation 712, the second teeth image is transmitted to a display device to display the second teeth image on the screen of the display device. For example, the image processing device 200 uses the wireless device 210 to transmits the second teeth image to the display device through the network (e.g., the network 150), so that the display device can display the second teeth image on the screen of the display device.

The terminology used herein is for the purpose of describing particular embodiments only, and is not intended to be limiting of the invention. As used herein, the singular forms "a", "an" and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

What is claimed is:

1. An image processing method for a fluorescence reaction region of teeth, comprising:
    emitting blue light from a light source to illuminate the teeth in a mouth, so that the teeth generate fluorescence;
    capturing a first teeth image of the teeth by an image capturing unit;
    separating the first teeth image into a first red-value image, a first green-value image, and a first blue-value image by a processing unit;
    transforming the first red value image into a second red value image by the processing unit using a pixel value transforming function,
    wherein in the step of transforming the first red-value image into the second red-value image, further decreasing a red pixel value of the first red-value image that is smaller than a predetermined value, and increasing a red pixel value that is greater than the predetermined value,
    wherein an upper limit of the increased red pixel value of the first red-value image is 2n−1, and a lower limit of the decreased red pixel value of the first red-value image is 0, where n is a positive integer; and
    combining the second red-value image, the first green-value image, and the first blue-value image into a second teeth image by the processing unit.

2. The method as claimed in claim 1, further comprising:
    transmitting the second teeth image to a display device to display the second teeth image.

3. The method as claimed in claim 1, wherein the step of transforming the first red-value image into the second red-value image further comprises:
    generating a red pixel value correspondence table with the pixel value transforming function using the red pixel values from 0 to 2n−1; and
    transforming the first red-value image into the second red-value image according to the red pixel value correspondence table.

4. The method as claimed in claim 1, wherein:
    the step of reducing the red pixel value that is smaller than the predetermined value is to subtract a first transformed red pixel value from the red pixel value that is smaller than the predetermined value, wherein the first transformed red pixel value is obtained by substituting the red pixel value that is smaller than the predetermined value into a first elliptic function; and the step of increasing the red pixel value that is greater than the predetermined value is to add a second transformed red pixel value to the red pixel value that is greater than the predetermined value plus, wherein the second transformed red pixel value is obtained by substituting the red pixel value that is greater than the predetermined value into a second elliptic function.

5. An image processing device for a fluorescence reaction region of teeth, comprising:

a light source, disposed to emit blue light to illuminate the teeth in a mouth, so that the teeth generate fluorescence;

an image capturing unit, disposed to capture a first teeth image of the teeth;

a processing unit, disposed to process the first teeth image, wherein the step in which the processing unit processes the first teeth image comprises:

separating the first teeth image into a first red-value image, a first green-value image, and a first blue-value image;

transforming the first red-value image into a second red-value image by using a pixel value transforming function, wherein in the step of transforming the first red-value image into the second red-value image, further decreasing a red pixel value of the first red-value image that is smaller than a predetermined value, and increasing a red pixel value that is greater than the predetermined value, wherein an upper limit of the increased red pixel value of the first red-value image is 2n−1, and a lower limit of the decreased red pixel value of the first red-value image is 0, where n is a positive integer; and combining the second red-value image, the first green-value image, and the first blue-value image into a second teeth image.

6. The image processing device as claimed in claim 5, further comprising:

a storage device, storing the pixel value transforming function and a red pixel value correspondence table, wherein the processing unit transforms the first red-value image into the second red-value image according to the red pixel value correspondence table.

7. The image processing device as claimed in claim 5, wherein the pixel value transforming function comprises:

a first elliptic function, performed by the processing unit to decrease the red pixel value that is smaller than the predetermined value, wherein the processing unit substitutes the red pixel value that is smaller than the predetermined value into the first elliptic function to obtain a first transformed red pixel value, and then subtracts the first transformed red pixel value from the red pixel value that is smaller than the predetermined value; and a second elliptic function, performed by the processing unit to increase the red pixel value that is greater than the predetermined value, wherein the processing unit substitutes the red pixel value that is greater than the predetermined value into the second elliptic function to obtain a second transformed red pixel value, and then adds the second transformed red pixel value to the red pixel value that is greater than the predetermined value.

* * * * *